United States Patent
Black et al.

(10) Patent No.: US 7,993,352 B2
(45) Date of Patent: Aug. 9, 2011

(54) ELECTRICAL STIMULATION SYSTEM AND ASSOCIATED APPARATUS FOR SECURING AN ELECTRICAL STIMULATION LEAD IN POSITION IN A PERSON'S BRAIN

(75) Inventors: Damon R. Black, Dallas, TX (US); Terry D. Daglow, Allen, TX (US); Robert E. Jones, McKinney, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 1808 days.

(21) Appl. No.: 11/010,108

(22) Filed: Dec. 10, 2004

(65) Prior Publication Data
US 2005/0143799 A1 Jun. 30, 2005

Related U.S. Application Data

(60) Provisional application No. 60/528,604, filed on Dec. 11, 2003.

(51) Int. Cl.
*A61B 19/00* (2006.01)
(52) U.S. Cl. ............................................. 606/129
(58) Field of Classification Search .................. 606/129, 606/130, 72–75, 103; 604/48; 245/1.5; 174/152 G, 174/153 G
See application file for complete search history.

(56) References Cited

U.S. PATENT DOCUMENTS

| | | | |
|---|---|---|---|
| 5,902,236 A | 5/1999 | Iversen | 600/377 |
| 5,927,277 A * | 7/1999 | Baudino et al. | 606/129 |
| 5,954,687 A * | 9/1999 | Baudino | 604/48 |
| 6,011,996 A | 1/2000 | Gielen et al. | 607/116 |
| 6,091,979 A | 7/2000 | Madsen | 600/377 |
| 6,210,417 B1 * | 4/2001 | Baudino et al. | 606/129 |
| 6,301,492 B1 | 10/2001 | Zonenshayn | 600/378 |
| 6,606,521 B2 | 8/2003 | Paspa et al. | 607/116 |
| 7,204,840 B2 * | 4/2007 | Skakoon et al. | 606/129 |
| 2005/0143800 A1 | 6/2005 | Lando et al. | 607/116 |
| 2005/0246004 A1 | 11/2005 | Cameron et al. | 607/116 |

* cited by examiner

*Primary Examiner* — Julian W Woo
(74) *Attorney, Agent, or Firm* — Christopher S. L. Crawford; Craig Hoersten; Melissa Acosta (57) ABSTRACT

In one aspect, an apparatus is provided for securing an electrical stimulation lead in position in a person's brain. The apparatus includes a body configured to seat within a burr hole formed in the person's skull. The apparatus also includes a central elastic membrane coupled to the body and extending across a central aperture of the body. The elastic membrane includes a number of pre-formed openings provided for purposes of securing the lead in position within the brain after implantation. Each pre-formed opening may penetrate through an entire thickness of the elastic membrane. Each pre-formed opening may be selected for insertion of the lead into the brain. Each pre-formed opening is adapted to elastically expand as the lead is inserted through the pre-formed opening and positioned in the brain and is adapted to elastically contract on the lead to secure the lead in position within the brain after implantation.

11 Claims, 5 Drawing Sheets

ELECTRICAL STIMULATION SYSTEM AND ASSOCIATED APPARATUS FOR SECURING AN ELECTRICAL STIMULATION LEAD IN POSITION IN A PERSON'S BRAIN

RELATED APPLICATIONS

This application claims the benefit under 35 U.S.C. §119(e) of U.S. Provisional Application Ser. No. 60/528,604, filed Dec. 11, 2003.

TECHNICAL FIELD OF THE INVENTION

This invention relates generally to electrical stimulation systems designed for implantation into a person's body and more particularly to an electrical stimulation system and associated apparatus for securing an electrical stimulation lead in position in a person's brain.

BACKGROUND

Electrical energy is applied to the brain to treat a variety of clinical conditions such as movement disorders or chronic pain. One method of delivering electrical energy to the brain involves inserting an electrical stimulation lead through a burr hole formed in the skull and then positioning the lead in a precise location adjacent a target area of the brain to be stimulated such that stimulation of the target area causes a desired clinical effect. For example, one desired clinical effect may be cessation of tremor from a movement disorder such as Parkinson's Disease. A variety of other clinical conditions may also be treated with deep brain stimulation, such as essential tremor, tremor from multiple sclerosis or brain injury, or dystonia or other movement disorders. The electrical stimulation lead implanted in the brain is connected to an electrical signal generator implanted at a separate site in the body, such as in the upper chest.

Electrical stimulation leads implanted in the brain require precise placement because of the relatively small size of the target area in the brain and because of the relatively close proximity of other non-targeted anatomic regions in the brain. One method of achieving precise placement is through a stereotactic surgical procedure that uses radiographic or fluoroscopic images of the brain to guide the surgeon to the target area. This may require placement of a three-dimensional frame to the head such that horizontal and vertical coordinates of the target area may be compared to radiographic images and precisely located. Other stereotactic methods may include a frameless procedure. Once the precise location of an electrical stimulation lead in the brain is achieved it is important that the lead remain in its precise position to avoid injury to the brain, reduced effectiveness, or other undesirable effects. An electrical stimulation lead may be particularly prone to being dislodged when a stereotactic frame is disassembled and removed from the head, for example, after insertion of the lead. When the frame is being disassembled and removed from around the insertion site, a doctor, nurse, or other clinician must typically attempt to manually secure the exposed end of the electrical stimulation lead in an attempt to maintain the precise positioning of the lead in the brain. This is difficult, if not impossible, to accomplish in practice.

Previous burr hole covers used for securing an electrical stimulation lead in position in a person's brain have included a fluid-impermeable membrane that spans the entire central aperture of the burr hole cover to prevent leakage of cerebrospinal fluid (CSF) from the brain. In these previous burr hole covers the fluid-impermeable membrane has been solid and the electrical stimulation lead is forced through the fluid-impermeable membrane to form a puncture hole in which the lead is then secured. Certain of these previous fluid-impermeable membranes have included an upper portion with one or more pre-formed blind holes above the solid lower portion that is punctured to form a hole for securing the electrical stimulation lead. With or without blind holes, when the electrical stimulation lead is secured in the puncture hole, the fit of the lead within the puncture hole and the fluid-impermeable nature of the surrounding membrane prevent CSF leakage from the brain. The puncture hole formed through the fluid-impermeable membrane, and any associated blind hole, is preferably sized such that upon removal of the electrical stimulation lead the fluid-impermeable membrane reseals and CSF leakage continues to be prevented.

SUMMARY OF THE INVENTION

In one aspect, an apparatus is provided for securing an electrical stimulation lead in position in a person's brain. The apparatus includes a body configured to seat within a burr hole formed in the person's skull. The apparatus also includes a central elastic membrane coupled to the body and extending across a central aperture of the body. The elastic membrane includes a number of pre-formed openings provided for purposes of securing the lead in position within the brain after implantation. Each pre-formed opening may penetrate through an entire thickness of the elastic membrane. Each pre-formed opening may be selected for insertion of the lead into the brain. Each pre-formed opening is adapted to elastically expand as the lead is inserted through the pre-formed opening and positioned in the brain and is adapted to elastically contract on the lead to secure the lead in position within the brain after implantation.

In another aspect, a method is provided for securing an electrical stimulation lead in position in a person's brain. The method includes inserting an apparatus into a burr hole formed in the person's skull. A body of the apparatus is configured to seat within the burr hole. A central elastic membrane of the apparatus extends across a central aperture of the apparatus body. The elastic membrane includes a number of pre-formed openings provided for purposes of securing the lead in position within the brain. Each pre-formed opening may penetrate through an entire thickness of the elastic membrane. Each pre-formed opening is selectable for insertion of the lead into the brain. Each pre-formed opening is adapted to elastically expand to receive the lead as the lead is inserted through the pre-formed opening and positioned in the brain and is adapted to elastically contract on the lead to secure the lead in position within the brain after implantation. The method further includes inserting the lead through a selected pre-formed opening and positioning the lead within the brain. The selected pre-formed opening elastically expands as the lead is inserted through the selected pre-formed opening and positioned in the brain. The selected pre-formed opening elastically contracts on the lead to secure the lead in position within the brain after implantation.

In another aspect, an electrical stimulation system is provided for stimulating a person'brain using an electrical stimulation lead implanted in the person'body The system includes an electrical stimulation lead adapted for implantation in the brain through a burr hole formed in the person's skull, the lead including one or more electrodes operable to stimulate the brain. The system also includes an apparatus for securing the electrical stimulation lead after implantation of the lead in the brain. The apparatus includes a body configured to seat within the burr hole. The apparatus also includes a central elastic membrane coupled to the body and extending across a central aperture of the apparatus body. The elastic membrane includes a number of pre-formed openings provided for purposes of securing the lead in position within the brain after implantation. Each pre-formed opening may penetrate through an entire thickness of the elastic membrane. Each pre-formed opening is selectable for insertion of the lead into the brain. Each pre-formed opening is adapted to elastically expand as the lead is inserted through the pre-formed opening and positioned in the brain and is adapted to elastically contract on the lead to secure the lead in position within the brain after implantation. The system further includes an implantable stimulation source adapted to be coupled to the electrical stimulation lead and to generate electrical signals for transmission to the lead for stimulation of the brain.

In another aspect, a method is provided for implanting an electrical stimulation system into a person's body for stimulating the person's brain using an electrical stimulation lead implanted in the person's brain. The method includes inserting an apparatus into a burr hole formed in the person's skull. A body of the apparatus is configured to seat within the burr hole. A central elastic membrane of the apparatus extends across a central aperture of the apparatus body. The elastic membrane includes a number of pre-formed openings provided for purposes of securing the lead in position within the brain. Each pre-formed opening may penetrate through an entire thickness of the elastic membrane. Each pre-formed opening is selectable for insertion of the lead into the brain. Each pre-formed opening is adapted to elastically expand to receive the lead as the lead is inserted through the pre-formed opening and positioned in the brain and is adapted to elastically contract on the lead to secure the lead in position within the brain after implantation. The method also includes inserting the lead through a selected pre-formed opening and positioning the lead within the brain. The selected pre-formed opening elastically expands as the lead is inserted through the selected pre-formed opening and positioned in the brain. The selected pre-formed opening elastically contracts on the lead to secure the lead in position within the brain after implantation. The method further includes implanting into the person's body a stimulation source adapted to be coupled to the lead and to generate electrical signals for transmission to the lead for stimulation of the brain.

Certain embodiments of the present invention may provide one or more technical advantages. In contrast to previous burr hole covers, the apparatus of the present invention provides an elastic membrane including one or more pre-formed openings that penetrate the entire thickness of the membrane and through which CSF may freely pass. In this embodiment, openings are formed in membrane solely for purposes of securing the electrical stimulation lead in position in the brain after implantation, without regard to CSF leakage. Significantly, the electrical stimulation lead may be simply and easily inserted through a selected pre-formed opening and secured in position as the membrane elastically contracts on the lead in the selected pre-formed opening. The electrical stimulation lead need not be physically forced through the membrane to form a puncture hole for securing the lead as with previous burr hole covers, which may reduce the risk of injury to the patient or damage to the lead or other medical equipment, may simplify the lead implantation procedure, and may provide one or more other benefits. One or more other technical advantages may be readily apparent to one skilled in the art from the figures, descriptions, and claims included herein.

BRIEF DESCRIPTION OF THE DRAWINGS

For a more complete understanding of the present invention and advantages thereof, reference is now made to the following description taken in conjunction with the accompanying drawings, in which.

DESCRIPTION OF EXAMPLE EMBODIMENTS

FIGS. 1A-2B illustrate an example apparatus 10 for securing an electrical stimulation lead in position in a person's brain, the lead implanted in the person's brain through a burr hole formed in the person's skull. For example, the burr hole may be formed to provide access to the brain for implantation of the electrical stimulation lead for deep brain or other brain stimulation, and apparatus 10 may be used to secure the lead during and after precise positioning of the lead in the brain using a stereotactic or other surgical procedure. The electrical stimulation lead may be a percutaneous lead having one or more circumferential electrodes that emit electrical energy substantially radially in all directions, a laminotomy or "paddle style" lead having one or more directional electrodes that emit electrical energy in a direction substantially perpendicular to a surface of the lead, or any other suitable lead. As described more fully below, the electrodes of the electrical stimulation lead are located at one or more sites along a stimulating portion of the lead having a leading end that enters the skull first and a trailing end that enters the skull thereafter. A connecting portion of the electrical stimulation lead typically couples the stimulating portion of the lead to an appropriate source of electrical stimulation that drives the electrodes of the lead.

Figure 1A:
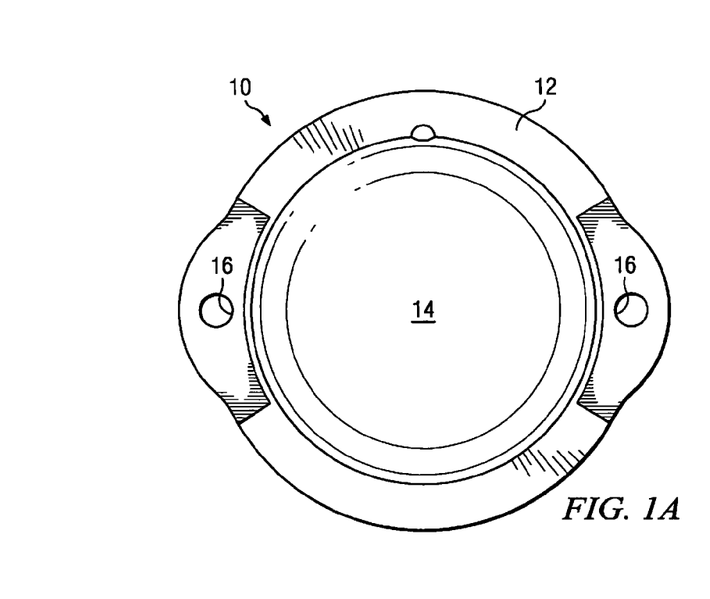
FIG. 1A illustrates a top view of an example apparatus for securing an electrical stimulation lead in position in a person's brain.
Figure 1B:
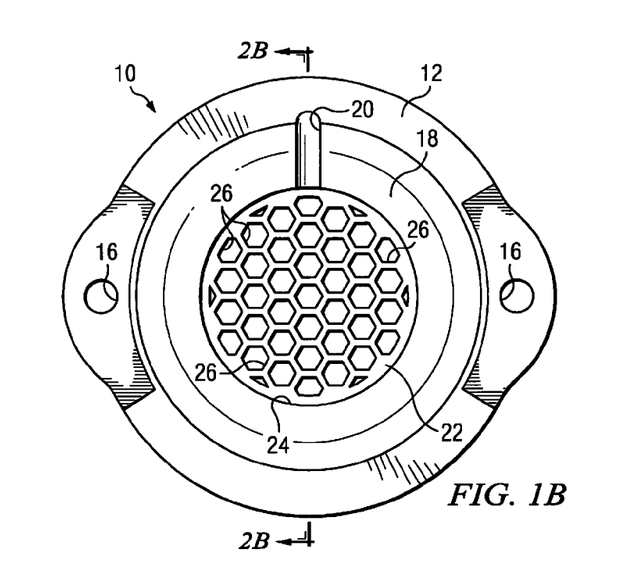
FIG. 1B illustrates a top view of an example apparatus for securing an electrical stimulation lead in position in a person's brain, with its cap removed.
Figure 2A:
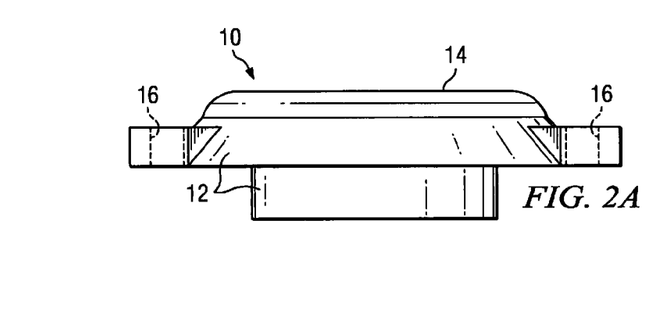
FIG. 2A illustrates a side view of an example apparatus for securing an electrical stimulation lead in position in a person's brain.
Figure 2B:
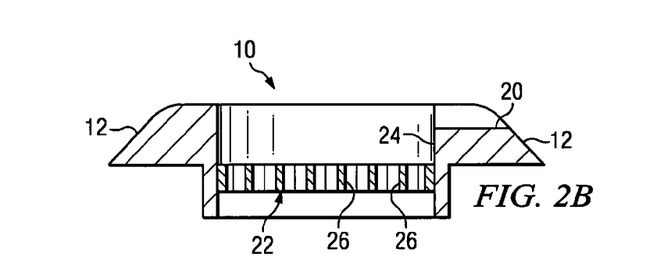
FIG. 2B illustrates a cross-sectional view of an example apparatus for securing an electrical stimulation lead in position in a person's brain, with its cap removed.

In one embodiment, apparatus 10 includes a substantially ring-shaped body 12 and a substantially circular cap 14. In other embodiments, body 12 and cap 14 may have other suitable shapes. Body 12 is configured to seat within the burr hole formed in the skull. Body 12 may include one or more holes 16 through which sutures, screws, or other suitable fixators may be placed to secure body 12 to the scalp or skull. Cap 14 is configured to be removably inserted into and to seat within body 12 to secure in position an electrical stimulation lead implanted in the brain. FIGS. 1A and 2A show body 12 with cap 14 attached. As shown in FIGS. 1B and 2B with cap 14 removed, body 12 may include a suitable indentation 18 into which cap 14 may be snapped, force-fitted, or otherwise removably secured. Body 12 may include one or more substantially transverse channels 20 configured to receive the connecting portion of the electrical stimulation lead such that the connecting portion is positioned in a channel 20 to lay substantially flat along the skull before being covered over with cap 14. Although a single channel 20 is shown, multiple channels 20 may be provided to allow the electrical stimulation lead to be positioned in a selected channel 20 closest to the location of the lead within the burr hole. Body 12 and cap 14 may be formed of a biocompatible polymer, plastic, rubber, metal or any other suitable material. In one embodiment, body 12 and cap 14 may be referred to collectively as a "burr hole cover" or "burr hole cap."

As shown in FIGS. 1B and 2B, a central elastic membrane 22 is coupled to the side of and extends across a central aperture 24 of body 12. Membrane 22 includes one or more pre-formed openings 26 through which CSF may freely pass. Openings 26 may have regular (i.e. circles, triangles, squares, hexagons, etc.), irregular, or any other suitable shapes and may be spaced in a regular pattern, irregularly, or in any other suitable manner. Each opening 26 preferably penetrates the entire thickness of membrane 22 and is smaller than the diameter of the stimulating portion of the electrical stimulation lead and any associated insertion cannula, such as a cannula associated with a needle. In one embodiment, all openings 26 have substantially the same size and shape. In a more particular embodiment, the electrical stimulation lead a width of approximately $55/1000$ inch and each opening 26 has a natural width of approximately $30/1000$ inch and is adapted to expand to a width of at least approximately $55/1000$ inch to receive and secure the lead, as described more fully below. However, the present invention contemplates one or more openings 26 being sized and shaped differently than one or more other openings 26. Membrane 22 may be formed of any suitable biocompatible elastomer, polymer, polyurethane, rubber or other material.

In one embodiment, openings 26 are formed in elastic membrane 22 solely for purposes of securing the electrical stimulation lead in position in the brain after implantation. Each opening 26 is selectable for insertion of the electrical stimulation lead into the brain, is adapted to elastically expand as the lead is inserted through opening 26 and positioned in the brain, and is also adapted to elastically contract on the lead to secure the lead in position in the brain after implantation. Where an insertion cannula is used for insertion of the electrical stimulation lead, this means that each opening 26 is: (1) selectable for insertion of the cannula into the brain, the lead being inserted into the brain via the cannula; (2) adapted to elastically expand to receive the cannula as the cannula is inserted through opening 26 and positioned in the brain, the lead being inserted through opening 26 via the cannula and positioned in the brain via cannula 26; and (3) adapted to elastically contract on and continuously grip the cannula until the cannula is removed from the brain after implantation of the lead and, substantially immediately after the cannula is removed, to elastically contract on and continuously grip the lead to secure the lead in position in the brain. For example, a hollow needle may provide such a cannula.

Previous burr hole covers used for securing an electrical stimulation lead in position in a person's brain have included a fluid-impermeable membrane that spans the entire central aperture of the burr hole cover to prevent leakage of CSF from the brain. In these previous burr hole covers the fluid-impermeable membrane has been solid such that the electrical stimulation lead must be physically forced through the fluid-impermeable membrane to form a puncture hole in which the lead is thereafter the secured. Certain of these previous fluid-impermeable membranes have included an upper portion with one or more pre-formed blind holes above the solid lower portion that must be punctured to form the hole for securing the electrical stimulation lead. With or without blind holes, when the electrical stimulation lead is secured in the puncture hole, the fit of the lead in the puncture hole and the fluid-impermeable nature of the surrounding membrane prevent CSF leakage. The puncture hole formed through the fluid-impermeable membrane, and any associated blind hole, is preferably sized such that upon removal of the electrical stimulation lead the fluid-impermeable membrane reseals and CSF leakage continues to be prevented.

In contrast, apparatus 10 provides an elastic membrane 22 including one or more pre-formed openings 26 that penetrate the entire thickness of membrane 22 and through which CSF may freely pass. In this embodiment, openings 26 are formed in membrane 22 solely for purposes of securing the electrical stimulation lead in position in the brain after implantation, without regard to any CSF leakage. Significantly, the electrical stimulation lead may be simply and easily inserted through a selected pre-formed opening 26 and secured in position as membrane 22 elastically contracts on the lead within the selected pre-formed opening 26. The electrical stimulation lead need not be physically forced through membrane 22 to form a puncture hole for securing the lead as with previous burr hole covers, which may reduce the risk of injury to the patient or damage to the lead or other medical equipment, may simplify the overall procedure, and may provide one or more other benefits.

Figure 3A:
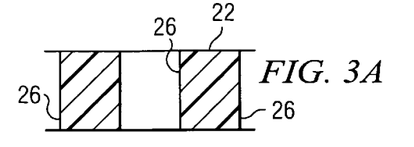
FIGS. 3A-3F illustrate an example of using an opening in an elastic membrane of the apparatus of FIGS. 1A-2B to secure an electrical stimulation lead in position in a person's brain.
Figure 3B:
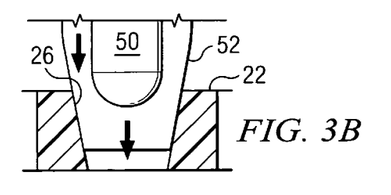
Figure 3C:
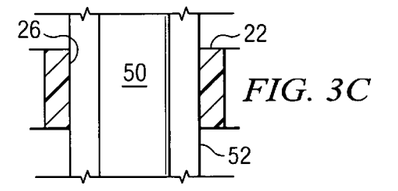
Figure 3D:
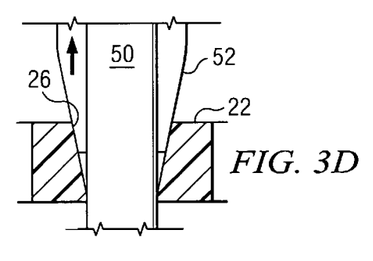
Figure 3E:
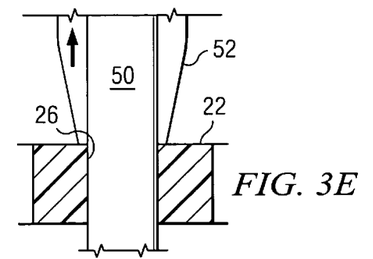
Figure 3F:
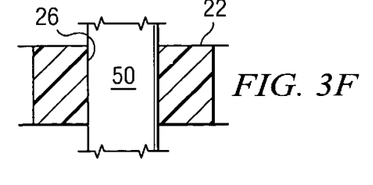

FIGS. 3A-3F illustrate an example of using an opening 26 in elastic membrane 22 to secure an electrical stimulation lead in position in the brain. In one embodiment, as shown in FIGS. 3A-3B, a particular opening 26 is selected for insertion of the electrical stimulation lead 50 and any associated insertion cannula 52 according to the desired position of lead 50 within the burr hole. Typically, as shown in FIGS. 3B-3C, cannula 52 is inserted into the selected opening 26 and advanced to the desired depth such that a leading end of cannula 52 is positioned in the brain in appropriate proximity to the target area to be stimulated. Electrical stimulation lead 50 may be inserted along with cannula 52 as shown. Alternatively, electrical stimulation lead 50 may be inserted through cannula 52 after insertion of cannula 52. In either case, the leading end of the stimulating portion of electrical stimulation lead 50 is positioned within the leading end of cannula 52 and the stimulating portion as a whole is positioned adjacent the target area. The selected opening 26 elastically contracts on and continuously grips cannula 52 throughout this procedure, such that once electrical stimulation lead 50 has been positioned in the brain, that position may be precisely maintained. As shown in FIGS. 3D-3F, cannula 52 is then removed, leaving electrical stimulation lead 50 in position in the brain. The selected opening 26 elastically contracts on and continuously grips cannula 52 while cannula 52 is being removed, maintaining the precise positioning of electrical stimulation lead 50 in the brain. Substantially immediately after cannula 52 has been fully removed, the selected opening 26 elastically contracts on and continuously grips the trailing end of the stimulating portion of electrical stimulation lead 50, continuing to maintain the precise positioning of lead 50 in the brain. In one embodiment, membrane 22 is adapted to stretch to allow an opening 26 to move from its natural position to receive and secure electrical stimulation lead 50 and its associated insertion cannula 52, providing additional flexibility with respect to positioning of lead 50 within the burr hole.

In one embodiment, the pre-formed openings 26 in elastic membrane 22 are provided solely for maintaining the precise positioning of electrical stimulation lead 50 in the brain. In this embodiment, openings 26 are not provided to help prevent potential leakage of cerebral-spinal fluid or other substances out of the brain through openings 26 and openings 26 are not intentionally sized to help prevent such leakage. However, in other embodiments, openings 26 may be sized both to help maintain the precise positioning of electrical stimulation lead 50 in the brain and to help prevent leakage of cerebral-spinal fluid or other substances out of the brain.

Figure 4A:
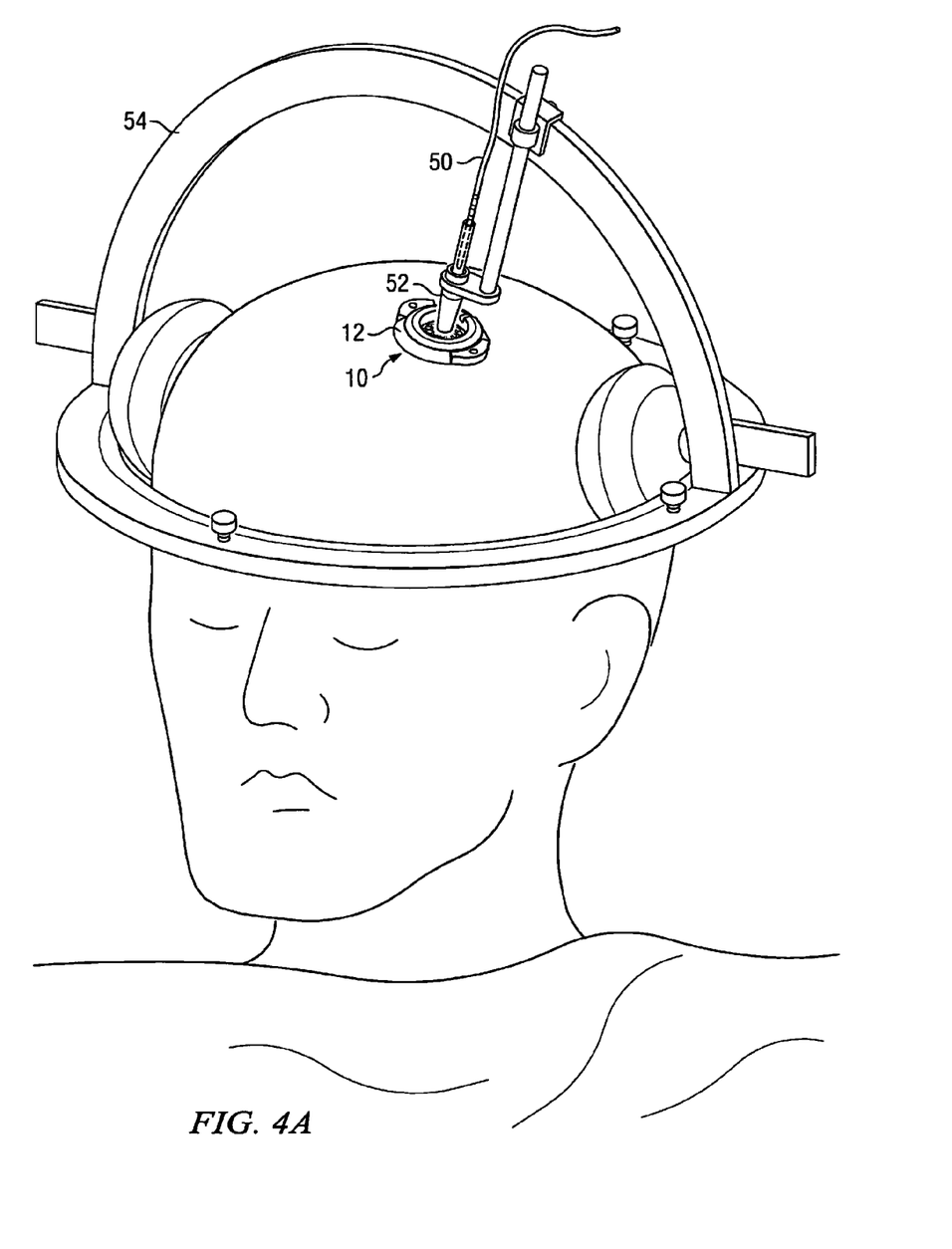
FIGS. 4A-4C illustrate an example of a person undergoing placement of an electrical stimulation lead using the apparatus of FIGS. 1A-2B.
Figure 4B:
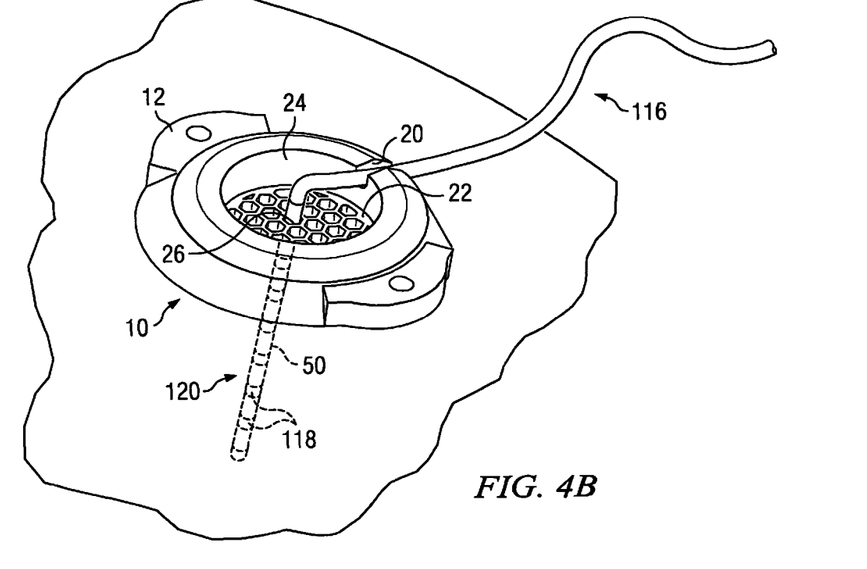
Figure 4C:
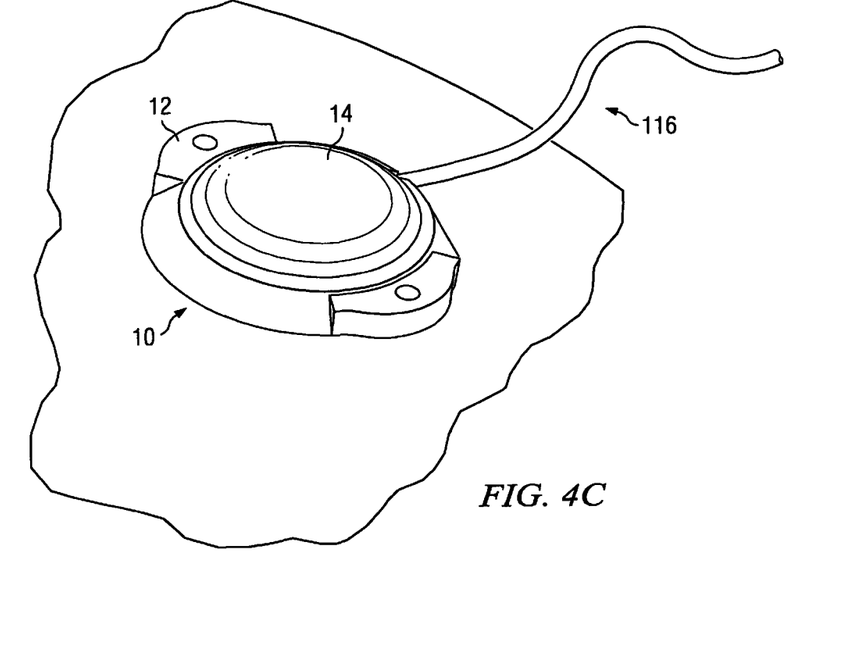

FIGS. 4A-4C illustrate an example of a person undergoing placement of an electrical stimulation lead 50 for brain stimulation using stereotactic equipment 54 to guide lead placement and apparatus 10 to secure lead 50 in position in the person's brain. As can be appreciated from FIG. 4A, the electrical stimulation lead 50 is typically coupled to stereotactic equipment 54 during lead placement for increased stability and housed within an insertion cannula 52 for insertion into the brain. Using prior techniques, the precise positioning of electrical stimulation lead 50 in the brain may be easily disturbed when lead 50 is uncoupled from stereotactic equipment 54 to allow cannula 52 to be removed from the brain. In contrast, according to the present invention, the selected pre-formed opening 26 in elastic membrane 22 of body 12 helps to secure electrical stimulation lead 50 in its precise position in the brain despite the uncoupling of lead 50 from stereotactic equipment 54 and removal of cannula 52 from the brain. FIG. 4B shows a close-up view of stimulating portion 112 of electrical stimulation lead 50, with electrodes 114, after insertion through a selected opening 26 in membrane 22 via cannula 52 and subsequent removal of cannula 52. The connecting portion 116 of electrical stimulation lead 50 is positioned in transverse channel 20 of body 12 to lay substantially flat on the skull. FIG. 4C shows a close-up view with removable cap 14 coupled to body 12 to secure electrical stimulation lead 50 in selected opening 26, to additionally secure the connecting portion of lead 50 in channel 20 where appropriate, and to additionally help prevent both leakage from the burr hole and entry of contaminants into the burr hole where appropriate.

Figure 5A:
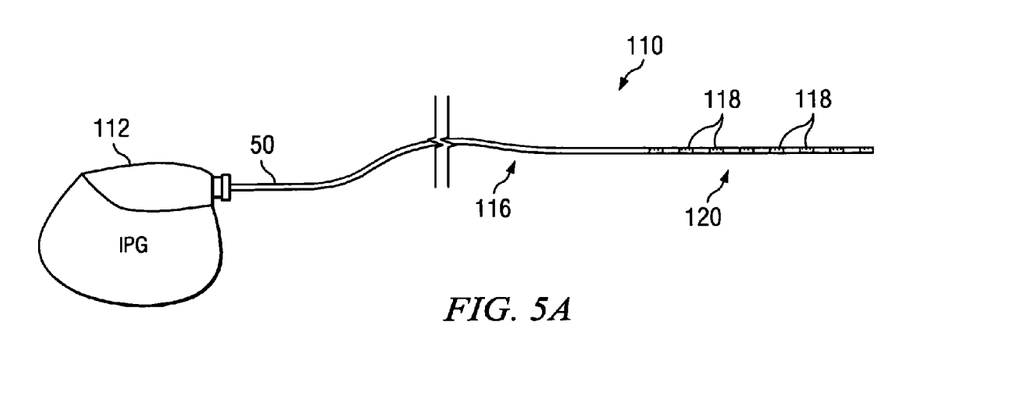
FIG. 5A illustrates an example electrical stimulation system including an implantable pulse generator.
Figure 5B:
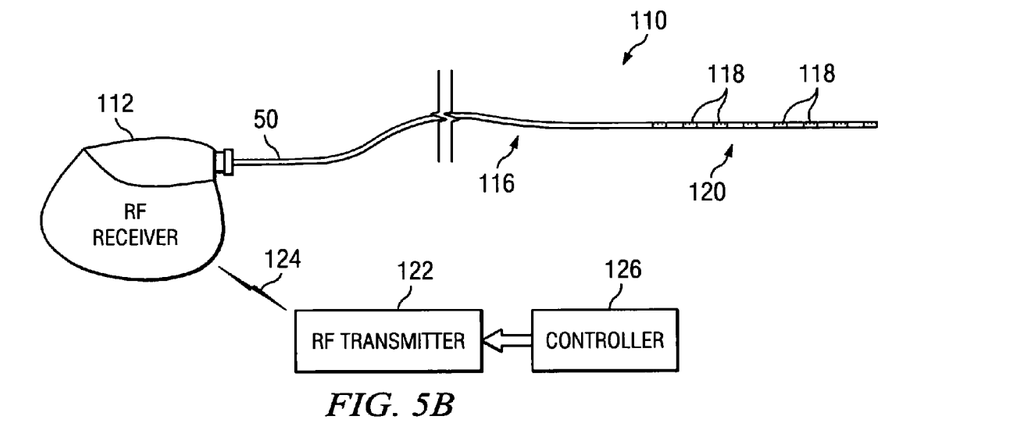
FIG. 5B illustrates an example electrical stimulation system including a wireless receiver.

FIGS. 5A-5B illustrate example electrical stimulation systems 110 for use with apparatus 10. Stimulation system 110 generates and applies a stimulus to a target area of a person's brain. In general terms, stimulation system 110 includes an implantable electrical stimulation source 112 and an implantable electrical stimulation lead 50 for applying the stimulation signal to the target brain tissue. In operation, both of these primary components are implanted in the person's body. Stimulation source 112 is coupled to a connecting portion 116 of electrical stimulation lead 50. Stimulation source 112 controls the electrical signals transmitted to electrodes 118 located on a stimulating portion 120 of electrical stimulation lead 50, located adjacent the target brain tissue, according to suitable signal parameters (e.g., duration, intensity, frequency, etc.). A doctor, the patient, or another user of stimulation source 112 may directly or indirectly input signal parameters for controlling the nature of the electrical stimulation provided.

In one embodiment, as shown in FIG. 5A, stimulation source 112 includes an implantable pulse generator (IPG). An example IPG may be one manufactured by Advanced Neuromodulation Systems, Inc., such as the Genesis® System, part numbers 3604, 3608, 3609, and 3644. In another embodiment, as shown in FIG. 5B, stimulation source 112 includes an implantable wireless receiver. An example wireless receiver may be one manufactured by Advanced Neuromodulation Systems, Inc., such as the Renew® System, part numbers 3408 and 3416. The wireless receiver is capable of receiving wireless signals from a wireless transmitter 122 located external to the person's body. The wireless signals are represented in FIG. 5B by wireless link symbol 124. A doctor, the patient, or another user of stimulation source 112 may use a controller 126 located external to the person's body to provide control signals for operation of stimulation source 112. Controller 126 provides the control signals to wireless transmitter 122, wireless transmitter 122 transmits the control signals and power to the wireless receiver of stimulation source 112, and stimulation source 112 uses the control signals to vary the signal parameters of the electrical signals transmitted through electrical stimulation lead 50 to the stimulation site. An example wireless transmitter 122 may be one manufactured by Advanced Neuromodulation Systems, Inc., such as the Renew® System, part numbers 3508 and 3516.

Figure 6:
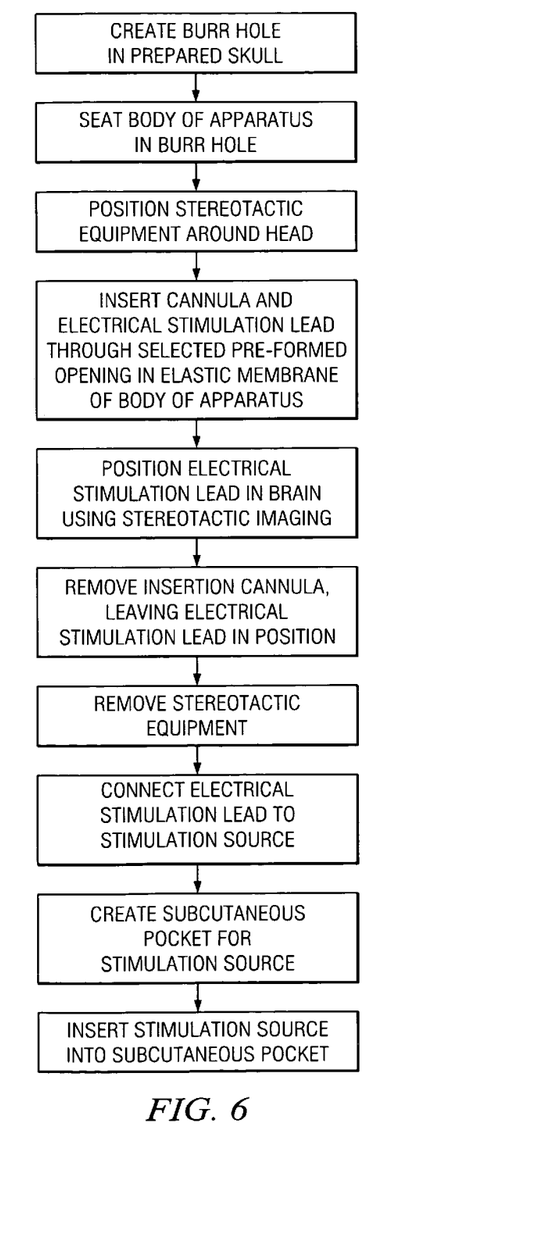
FIG. 6 illustrates example steps for implanting an electrical stimulation system into a person for electrical stimulation of the person's brain.

FIG. 6 illustrates example steps that may be used to implant an example stimulation system 110 into a person for electrical stimulation of the person's brain. The skull is first prepared by exposing the skull and creating a burr hole in the skull. Body 12 of apparatus 10 is then seated within the burr hole and fixed to the scalp or skull, for example, using holes 16. Stereotactic equipment 54 suitable to aid in the placement of electrical stimulation lead 50 in the brain may be positioned around the head. An insertion cannula 52 for electrical stimulation lead 50 is inserted through a selected pre-formed opening 26 in elastic membrane 22 of body 12. For example, a hollow needle may provide cannula 52. Cannula 52 and electrical stimulation lead 50 may be inserted together or lead 50 may be inserted through cannula 52 after cannula 52 has been inserted. Using stereotactic imaging guidance or otherwise, electrical stimulation lead 50 is then precisely positioned within the brain.

Once electrical stimulation lead 50 has been positioned in the brain, lead 50 is uncoupled from any stereotactic equipment 54, and cannula 52 and any stereotactic equipment 54 are removed. Where stereotactic equipment 54 is used, cannula 52 may be removed before, during, or after removal of stereotactic equipment 54. As cannula 52 is withdrawn, the selected opening 26 in membrane 22 contracts on and continuously grips cannula 52 to help maintain the precise positioning of electrical stimulation lead 50 in the brain. Substantially immediately after cannula 52 has been fully removed, the selected opening 26 contracts on and continuously grips electrical stimulation lead 50 to continue to help maintain the precise positioning of lead 50 in the brain. Connecting portion 116 of electrical stimulation lead 50 is placed into channel 20 within body 12 of apparatus 10 and laid substantially flat along the skull. Cap 14 of apparatus 10 is snapped, force-fitted, or otherwise coupled to body 12 to secure electrical stimulation lead 50 in the selected opening 26, to additionally secure connecting portion 116 of lead 50 in channel 20 where appropriate, and to additionally help prevent both leakage from the burr hole and entry of contaminants into the burr hole where appropriate.

Once electrical stimulation lead 50 has been inserted and secured, lead 50 extends from the lead insertion site to the implant site at which stimulation source 112 is implanted. The implant site is typically a subcutaneous pocket formed to receive and house stimulation source 112. The implant site is usually positioned a distance away from the insertion site, such as near the buttocks or another place in the torso area. Once all appropriate components of stimulation system 110 are implanted, these components may be subject to mechanical forces and movement in response to movement of the person's body. A doctor, the patient, or another user of stimulation source 112 may directly or indirectly input signal parameters for controlling the nature of the electrical stimulation provided.

Although example steps are illustrated and described, the present invention contemplates two or more steps taking place substantially simultaneously or in a different order. In addition, the present invention contemplates using methods with additional steps, fewer steps, or different steps, so long as the steps remain appropriate for implanting an example stimulation system 110 into a person for electrical stimulation of the person's brain.

Although the present invention has been described with several embodiments, a number of changes, substitutions, variations, alterations, and modifications may be suggested to one skilled in the art, and it is intended that the invention encompass all such changes, substitutions, variations, alterations, and modifications as fall within the spirit and scope of the appended claims.

What is claimed is:

1. A method for securing an electrical stimulation lead in position in a person's brain, comprising:
    inserting an apparatus into a burr hole formed in the person's skull, a body of the apparatus configured to seat within the burr hole, a central elastic membrane of the apparatus extending across a central aperture of the apparatus body, the elastic membrane comprising a plurality of pre-formed openings provided for purposes of securing the lead in position within the brain, each pre-formed opening penetrating through an entire thickness of the elastic membrane, each pre-formed opening being selectable for insertion of the lead into the brain, each pre-formed opening being adapted to elastically expand to receive the lead as the lead is inserted through the pre-formed opening and positioned in the brain and being adapted to elastically contract on the lead to secure the lead in position within the brain after implantation; and
    inserting the lead through a selected pre-formed opening and positioning the lead within the brain, the selected pre-formed opening elastically expanding as the lead is inserted through the selected pre-formed opening and positioned in the brain, the selected pre-formed opening elastically contracting on the lead to secure the lead in position within the brain after implantation.

2. The method of claim 1, wherein the pre-formed openings in the elastic membrane are arranged in a substantially regular pattern across a substantial portion of the central elastic membrane.

3. The method of claim 1, wherein each pre-formed opening in the elastic membrane has the same regular geometric shape.

4. The method of claim 1, wherein:
    each pre-formed opening in the elastic membrane has a natural position; and
    the elastic membrane is adapted to stretch to allow a pre-formed opening to move from its natural position for insertion and positioning of the lead.

5. The method of claim 1, wherein:
    each pre-formed opening being selectable for insertion of the lead into the brain comprises being selectable for insertion of a cannula into the brain, the lead being inserted into the brain via the cannula;
    each pre-formed opening being adapted to elastically expand as the lead is inserted and positioned comprises being adapted to elastically expand to receive the cannula as the cannula is inserted through the pre-formed opening and positioned in the brain, the lead being inserted through the pre-formed opening via the cannula and positioned in the brain via the cannula;
    each pre-formed opening being adapted to elastically contract comprises being adapted to elastically contract on and continuously grip the cannula until the cannula is removed from the brain after implantation of the lead and, substantially immediately after the cannula is removed, to elastically contract on and continuously grip the lead to secure the lead in position within the brain;
    inserting and positioning the lead comprises inserting the lead through the selected pre-formed opening via the cannula and positioning the lead within the brain via the cannula;
    the selected pre-formed opening elastically expanding as the lead is inserted and positioned comprises elastically expanding to receive the cannula as the cannula is inserted through the selected pre-formed opening and positioned in the brain, the lead being inserted through the selected pre-formed opening via the cannula and positioned in the brain via the cannula; and
    the selected pre-formed opening elastically contracting comprises elastically contracting on and continuously gripping the cannula until the cannula is removed from the brain after implantation and, substantially immediately after the cannula is removed, elastically contracting on and continuously gripping the lead to secure the lead in position within the brain.

6. The method of claim 5, wherein if the lead is temporarily coupled to stereotactic equipment that is coupled to the person's head for positioning of the lead in the brain, the selected pre-formed opening elastically contracts on and continuously gripping the cannula until the stereotactic equipment is also removed from the head after implantation of the lead.

7. The method of claim 1, further comprising receiving and securing a connecting portion of the lead in a substantially transverse channel in the apparatus body, the connecting portion of the lead adapted to couple the lead to a stimulation source.

8. The method of claim 1, further comprising removably coupling a cap of the apparatus to the apparatus body after implantation of the lead.

9. A method for securing an electrical stimulation lead in position in a person's brain, comprising:
    inserting an apparatus into a burr hole formed in the person's skull, a body of the apparatus configured to seat within the burr hole, the apparatus comprising a central membrane of elastic material that covers a central aperture of the apparatus body, the central membrane comprising a plurality of pre-formed openings provided for purposes of securing the lead in position within the brain, each pre-formed opening penetrating through an entire thickness of the central membrane, each pre-formed opening being selectable for insertion of the lead into the brain, each pre-formed opening being adapted to elastically expand to receive the lead as the lead is inserted through the pre-formed opening and positioned in the brain and being adapted to elastically contract on the lead to secure the lead in position within the brain after implantation; and
    inserting the lead through a selected pre-formed opening, the insertion of the lead providing sufficient force to cause the selected pre-formed opening to expand;

positioning the lead such that electrodes of the lead are disposed in a selected area of the brain to apply stimulation pulses to the selected area; and holding the lead, by applying a compressive elastic force from the selected pre-formed opening, to retain the lead in a position such that the electrodes of the lead are disposed in the selected area of the brain.

10. The method of claim 9, wherein the pre-formed openings in the central membrane are arranged in a two-dimensional pattern across a substantial portion of the central aperture.

11. The method of claim 9, wherein:

each pre-formed opening in the central membrane has a natural position; and the central membrane is adapted to stretch in any direction to allow a pre-formed opening to move from its natural position for insertion and positioning of the lead.

* * * * *